United States Patent [19]

Ivy et al.

[11] Patent Number: 5,013,726

[45] Date of Patent: May 7, 1991

[54] EXTERNAL ANALGESIC LOTION CONTAINING ACTIVE INGREDIENTS OF METHYL SALICYLATE AND CAMPHOR AND MENTHOL AND METHOD OF MAKING SUCH LOTION

[76] Inventors: Jeffery W. Ivy, 218 Collier, Grand Saline, Tex. 75140; Curtis E. Payne, 255 Holley St., Alba, Tex. 75410

[21] Appl. No.: 406,072

[22] Filed: Sep. 12, 1989

[51] Int. Cl.$^5$ .......................... A61K 9/06; A61K 9/10; A61K 33/24; A61K 35/78

[52] U.S. Cl. .................. 514/159; 424/DIG. 13; 514/783; 514/886; 514/887; 514/906; 514/969

[58] Field of Search ............... 424/DIG. 13; 514/159, 514/783, 886, 887, 906, 969

[56] References Cited

U.S. PATENT DOCUMENTS

| | | | |
|---|---|---|---|
| 4,657,763 | 4/1987 | Finkelstein | 424/131 |
| 4,725,438 | 2/1988 | Leazer | 514/969 |
| 4,784,849 | 11/1988 | Tutsky | 514/969 |
| 4,883,664 | 11/1989 | Sharkey | 514/969 |

FOREIGN PATENT DOCUMENTS

| | | |
|---|---|---|
| 2184525 | 12/1973 | France . |
| 2554715 | 5/1985 | France . |
| 85/01653 | 4/1985 | PCT Int'l Appl. . |
| 88/03810 | 6/1988 | PCT Int'l Appl. . |

*Primary Examiner*—Ronald W. Griffin
*Attorney, Agent, or Firm*—Harry C. Post, III

[57] ABSTRACT

An external analgesic lotion containing active ingredients of methyl salicylate and camphor and menthol to relieve pain in muscles, joints, or viscera distal at the site of application by stimulating cutaneous sensory receptors and a method of making such lotion and being made from camphor and menthol crystals.

8 Claims, No Drawings

EXTERNAL ANALGESIC LOTION CONTAINING ACTIVE INGREDIENTS OF METHYL SALICYLATE AND CAMPHOR AND MENTHOL AND METHOD OF MAKING SUCH LOTION

This invention relates to an externally applied lotion that causes irritation or mild inflammation of the skin for the purpose of relieving pain in muscles, joints, or viscera distal to the site of application by stimulating cutaneous sensory receptors and the method of making.

It is well known that certain external analgesic products containing 10 to 60 percent methyl salicylate, more than 3 percent to 11 percent camphor and 1.25 to 16 percent menthol, either singly or in combination, cause irritation or mild inflammation of the skin for the purpose of relieving pain in muscles, joints, or viscera distal to the site of application by stimulating depressing cutaneous sensory receptors.

Although camphor and menthol have been used in external analgesic products, their crystals have not been used in lotions because the crystals are immiscible with the solutions formed by the other ingredients used.

Accordingly, it is an object of the present invention to provide an external analgesic lotion containing active ingredients of methyl salicylate and camphor and menthol to relieve pain in muscles, joints, or viscera distal at the site of application by stimulating cutaneous sensory receptors and a method of making such lotion.

Further, it is an object of the present invention to provide an external analgesic lotion made from camphor and menthol crystals.

The external analgesic lotion of this invention has a pH of 5.5 to 6.0, has a strong odor, is gold yellow, has less than 10 microorganisms per gram and no pathogenic contamination.

Aloe powder, such as that sold under the name Aloe Vera Phytogel 1:199, is contained in the lotion in an amount of from 0.0018 to 0.0022 parts by weight of the lotion and, preferably, in an amount of about 0.002 parts by weight.

From 62.5510 to 76.4510 deionized water is contained in the lotion and the preferred amount used is 69.501 parts by weight.

Carboxy polymethylene, such as that sold by BF Goodrich under the name Carbopol 1342, is contained in the lotion in an amount of from 0.3150 to 0.3850 parts by weight and, preferably, in an amount of about 0.350 parts by weight.

Propylene glycol, such as that sold by ARCO Chemical Company under the name Propylene Glycol USP, is contained in the lotion in an amount of from 3.6000 to 4.4000 parts by weight and, preferably, in an amount of about 4.000 parts by weight.

Methyl hydroxybenzoate, such as that sold by NIPA Laboratories, Inc. under the name Nipa Esters methyl p-hydroxybenzoate, is contained in the lotion in an amount of from 0.1800 to 0.2200 parts by weight and, preferably, in an amount of about 0.200 parts by weight.

Disodium dihydrogen ethylenediaminetetraacetate (disodium EDTA), such as that sold by The Dow Chemical Company under the name Versene NA, is contained in the lotion in an amount of from 0.0900 to 0.1100 parts by weight and, preferably, in an amount of about 0.100 parts by weight.

Diethanolamine cetyl phosphate (DEA-Cetyl Phosphate), such as that sold by Givaudan Corporation under the name Amphisol, is contained in the lotion in an amount of from 0.6300 to 0.7700 parts by weight and, preferably, in an amount of about 0.700 parts by weight.

Stearic acid is contained in the lotion in an amount of from 1.0900 to 1.1000 parts by weight and, preferably, in an amount of about 1.000 parts by weight.

PEG-8 distearate is contained in the lotion in an amount of from 0.4500 to 0.5500 parts by weight and, preferably, is contained in the lotion in an amount of about 0.500 parts by weight.

$C_{12-15}$ alcohols benzoate, such as that sold by Finetex Inc. under the name Finsolv TN, is contained in the lotion in an amount of from 4.5000 to 5.6800 parts by weight and, preferably, in an amount of about 5.000 parts by weight.

Urea is contained in the lotion in an amount of from from 0.0900 to 0.1100 parts by weight and, preferably, in an amount of about 0.100 parts by weight.

Eucalyptus oil is contained in the lotion in an amount of from 1.8000 to 2.2000 parts by weight and, preferably, in an amount of about 2.000 parts by weight.

Methyl salicylate is contained in the lotion in an amount of from 9.0000 to 12.8000 parts by weight and, preferably, in an amount of about 10.000 parts by weight.

Camphor crystals are contained in the lotion in an amount of from 2.7000 to 3.3000 parts by weight and, preferably, in an amount of about 3.000 parts by weight.

Menthol crystals are contained in the lotion in an amount of from 2.2500 to 2.7500 parts by weight and, preferably, in an amount of about 2.500 parts by weight.

Jojoba oil, such as that sold by LIPO Chemicals, Inc. under the name Lipovol J, is contained in the lotion in an amount of from 0.0900 to 0.1100 parts by weight and, preferably, in an amount of about 0.100 parts by weight.

A blend in a 5 to 1 ratio of 1,000,000 International Units of vitamin A to 200,000 International Units of vitamin $D_3$, such as that sold by Roche Chemical Division, Hoffmann-La Roche Inc. under the name Liquid Vitamin A and $D_3$ Blends, is contained in the lotion in an amount of from 0.0900 to 0.1100 parts by weight and, preferably, in an amount of about 0.100 parts by weight.

Di-alpha tocopheryl acetate, such as that sold by Roche Chemical Division, Hoffmann-La Roche Inc. under the name Vitamin E USP. FCC. is contained in the lotion in an amount of from 0.0900 to 0.1100 parts by weight and, preferably, in an amount of about 0.100 parts by weight.

Ginseng American 1:1 PB (propylene glycol) is contained in the lotion in an amount of from 0.1800 to 0.2200 parts by weight and, preferably, in an amount of about 0.200 parts by weight.

Imidazolidinyl urea, such as that sold by Sutton Laboratories, Inc. under the name GERMALL 115, is contained in the lotion in an amount of from 0.1800 to 0.2200 parts by weight and, preferably, in an amount of about 0.200 parts by weight.

Triethanolamine is contained in the lotion in an amount of from 0.1800 to 0.2200 parts by weight and, preferably, in an amount of about 0.200 parts by weight.

A solution of 1 percent FD&C Yellow #5 in water is contained in the lotion in an amount from 0.0900 to 0.1100 parts by weight and, preferably, in an amount of about 0.100 parts by weight.

24 carat gold is contained in the lotion in an amount of from 0.0423 to 0.0517 parts by weight and, preferably, in an amount of about 0.047 parts by weight.

The following example describes the steps to be followed in manufacturing the lotion.

From 62.5510 to 76.4510 parts by weight deionized water is supplied in a stainless steel kettle equipped with a mixer and a heat exchanger attached to the kettle for heating or cooling the ingredients in the kettle.

From 0.3150 to 0.3850 parts by weight carboxy polymethylene is dusted onto the water and mixed into the water.

As soon as the carboxy polymethylene and water are smooth and uniform, from 0.0018 to 0.0022 parts by weight aloe powder, from 3.6000 to 4.4000 parts by weight propylene glycol, from 0.1800 to 0.2200 parts by weight methyl hydroxybenzoate and from 0.0900 to 0.1100 parts by weight disodium dihydrogen ethylenediaminetetraacetate are added and mixed into the smooth and uniform mixture while heating to a temperature of 75° C.

Upon reaching 75° C., from 0.6300 to 0.7700 parts by weight diethanolamine cetyl phosphate, from 1.0900 to 1.1000 parts by weight stearic acid, from 0.4500 to 0.5500 parts by weight PEG-8 distearate, from 2.7000 to 3.4800 parts by weight $C_{12-15}$ alcohols benzoate and from 0.0900 to 0.1100 parts by weight urea are mixed into the 75° C. mixture.

The 75° C. mixture is then cooled to 55° C.

A solution having a temperature of 55° C. and obtained from 1.8000 to 2.2000 parts by weight $C_{12-15}$ alcohols benzoate, from 1.8000 to 2.2000 parts by weight eucalyptus oil, from 9.0000 to 12.8000 parts by weight methyl salicylate, from 2.7000 to 3.3000 parts by weight camphor crystals and from 2.2500 to 2.7500 parts by weight menthol crystals is mixed into the 55° C. mixture.

The 55° C. mixture is then cooled to a temperature of no more than 45° C.

From 0.0900 to 0.1100 parts by weight jojoba oil, from 0.0900 to 0.1100 parts by weight of a blend in a 5 to 1 ratio of 1,000,000 International Units of vitamin A to 200,000 International Units of vitamin $D_3$, from 0.0900 to 0.1100 parts by weight of di-alpha tocopheryl acetate, from 0.1800 to 0.2200 parts by weight ginseng America 1:1 propylene glycol, from 0.1800 to 0.2200 parts by weight imidazolidinyl urea, from 0.1800 to 0.2200 parts by weight triethanolamine, from 0.0900 to 0.1100 parts by weight of a solution of 1 percent FD&C Yellow #5 in water and from 0.0423 to 0.0517 parts by weight 24 carat gold are then mixed into the 45° C. mixture.

Should the lotion have a pH value of less than 5.5, triethanolamine is added to the mixture until the ph value is between 5.5 and 6.0.

If desired, the solution added to the 55° C. mixture may be prepared by dissolving the crystalline matter (from 9.0000 to 12.8000 parts by weight methyl salicylate, from 2.7000 to 3.3000 parts by weight camphor crystals and from 2.2500 to 2.7500 parts by weight menthol crystals) in the liquid (from 1.800 to 2.2000 parts by weight $C_{12-15}$ alcohols benzoate and from 1.8000 to 2.2000 parts by weight $C_{12-15}$ alcohols benzoate and from 1.8000 to 2.2000 parts by weight eucalyptus oil) in a separate vessel and heating such mixture to a temperature where the mixture is a solution and no crystalline matter is visible and continuing to heat to the 55° C. temperature for adding to the other 55° C. solution.

The invention having been described, what is claimed is:

1. An external analgesic lotion, consisting essentially of: from 0.0018 to 0.0022 parts by weight aloe powder; from 62.5510 to 76.4510 parts by weight deionized water; from 0.3150 to 0.3850 parts by weight carboxy polymethylene; from 3.6000 to 4.4000 parts by weight propylene glycol; from 0.1800 to 0.2200 parts by weight methyl hydroxybenzoate; from 0.0900 to 0.1100 parts by weight disodium dihydrogen ethylenediaminetetraacetate; from 0.6300 to 0.7700 parts by weight diethanolamine cetyl phosphate; from 1.0900 to 1.1000 parts by weight stearic acid; from 0.4500 to 0.5500 parts by weight PEG-8 distearate; from 4.5000 to 5.6800 parts by weight $C_{12-15}$ alcohols benzoate: from 0.0900 to 0.1100 parts by weight urea; from 1.8000 to 2.2000 parts by weight eucalyptus oil; from 9.0000 to 12.8000 parts by weight methyl salicylate; from 2.7000 to 3.3000 parts by weight camphor crystals; from 2.2500 to 2.7500 parts by weight menthol crystals; from 0.0900 to 0.1100 parts by weight jojoba oil; from 0.0900 to 0.1100 parts by weight of a blend in a 5 to 1 ratio of 1,000,000 International Units of vitamin A to 200,000 International Units of vitamin $D_3$; from 0.0900 to 0.1100 parts by weight di-alpha tocopheryl acetate; from 0.1800 to 0.2200 parts by weight ginseng American 1:1 propylene glycol; from 0.1800 to 0.2200 parts by weight imidazolidinyl urea; from 0.1800 to 0.2200 parts by weight triethanolamine; from 0.0900 to 0.1100 parts by weight of a solution of 1 percent FD&C Yellow #5 in water; and from 0.0423 to 0.0517 parts by weight 24 carat gold.

2. A lotion as set forth in claim 1, consisting essentially of: about 0.002 parts by weight aloe powder; about 69.501 parts by weight deionized water; about 0.350 parts by weight carboxy polymethylene; about 4.000 parts by weight propylene glycol; about 0.200 parts by weight methyl hydroxybenzoate; about 0.100 parts by weight disodium dihydrogen ethylenediaminetetraacetate; about 0.700 parts by weight diethanolamine cetyl phosphate; about 1.000 parts by weight stearic acid; about 0.500 parts by weight PEG-8 distearate; about 5.000 parts by weight $C_{12-15}$ alcohols benzoate; about 0.100 parts by weight urea; about 2.000 parts by weight eucalyptus oil; about 10.000 parts by weight methyl salicylate; about 3.000 parts by weight camphor crystals; about 2.500 parts by weight menthol crystals; about 0.100 parts by weight jojoba oil; about 0.100 parts by weight of the blend in a 5 to 1 ratio of 1,000,000 International Units of vitamin A to 200,000 International Units of vitamin $D_3$; about 0.100 parts by weight di-alpha tocopheryl acetate; about 0.200 parts by weight ginseng America 1:1 propylene glycol; about 0.200 parts by weight imidazolidinyl urea: about 0.200 parts by weight triethanolamine; about 0.100 parts by weight of a solution of 1 percent FD&C Yellow #5 in water; and about 0.047 parts by weight 24 carat gold.

3. A lotion as set forth in claim 1, having: a pH of 5.5 to 6.0, a strong odor, being gold yellow, and having less than 10 microorganisms per gram and no pathogenic contamination.

4. A method of making an external analgesic lotion, comprising the steps of: heating from 62.5510 to 76.4510 parts by weight deionized water; continuously mixing from 0.3150 to 0.3850 parts by weight carboxy polymethylene into the water being heated until smooth and uniform, and then adding from 0.0018 to 0.0022 parts by weight aloe powder, from 3.6000 to 4.4000 parts by weight propylene glycol, from 0.1800 to 0.2200 parts by weight methyl hydroxybenzoate and from 0.0900 to 0.1100 parts by weight disodium dihydrogen ethylenediaminetetraacetate in the smooth and uniform mixture while heating to a temperature of 75° C.; mixing into the 75° C. mixture from 0.6300 to 0.7700 parts by weight diethanolamine cetyl phosphate, from 1.0900 to 1.1000 parts by weight stearic acid, from 0.4500 to 0.5500 parts by weight PEG-8 distearate, from 2.7000 to 3.4800 parts by weight $C_{12-15}$ alcohols benzoate and from 0.0900 to 0.1100 parts by weight urea; cooling the 75° C. mixture to 55° C.; mixing into the 55° C. mixture a solution having a temperature of 55° C. obtained from 1.8000 to 2.2000 parts by weight $C_{12-15}$ alcohols benzoate, from 1.8000 to 2.2000 parts by weight eucalyptus oil, from 9.0000 to 12.8000 parts by weight methyl salicylate, from 2.7000 to 3.3000 parts by weight camphor crystals and from 2.2500 to 2.7500 parts by weight menthol crystals until smooth and uniform; cooling the 55° C. mixture to no more than 45° C.; mixing into the 45° C. mixture from 0.0900 to 0.1100 parts by weight jojoba oil, from 0.0900 to 0.1100 parts by weight of a blend in a 5 to 1 ratio of 1,000,000 International Units of vitamin A to 200,000 International Units of vitamin $D_3$, from 0.0900 to 0.1100 parts by weight di alpha tocopheryl acetate, from 0.1800 to 0.2200 parts by weight ginseng America 1:1 propylene glycol, from 0.1800 to 0.2200 parts by weight imidazolidinyl urea, from 0.1800 to 0.2200 parts by weight triethanolamine, from 0.0900 to 0.1100 parts by weight of a solution of 1 percent FD&C Yellow #5 in water and from 0.0423 to 0.0517 parts by weight 24 carat gold.

5. A method as set forth in claim 4, further comprising the step of: adjusting the pH value of the lotion to between 5.5 and 6.0.

6. A method as set forth in claim 4, further comprising the step of: dissolving the crystalline matter in the liquid in a separate vessel to obtain the solution mixed into the 55° C. mixture while heating the mixture to a temperature of 55° C. until the mixture is a solution and no crystalline matter is visible.

7. An external analgesic lotion made by: heating and mixing about 0.350 parts by weight carboxy polymethylene in about 69.501 parts by weight deionized water until smooth and uniform, continuously heating and mixing about 0.002 parts by weight aloe powder, about 4.000 parts by weight propylene glycol, about 0.200 parts by weight methyl hydroxybenzoate, about 0.100 parts by weight disodium dihydrogen ethylenediaminetetraacetate into the smooth and uniform mixture until heated to a temperature of 75° C.; mixing into the 75° C. mixture about 0.700 parts by weight diethanolamine cetyl phosphate, about 1.000 parts by weight stearic acid, about 0.5000 parts by weight PEG-8 distearate, about 3.000 parts by weight $C_{12-15}$ alcohols benzoate and about 0.100 parts by weight urea; cooling the 75° C. mixture to 55° C.; in a separate vessel, heating and dissolving about 10.000 parts by weight methyl salicylate, about 3.000 parts by weight camphor crystals and about 2.500 parts by weight menthol crystals in about 2.000 parts by weight $C_{12-15}$ alcohols benzoate and about 2.000 parts by weight eucalyptus oil until smooth and uniform and at a temperature of 55° C.; mixing into the 55° C. mixture the 55° C. solution; cooling the 55° C. mixture and solution to a temperature of 45° C. and less; mixing into the 45° C. mixture and solution about 0.100 parts by weight jojoba oil; about 0.100 parts by weight of the blend in a 5 to 1 ratio of 1,000,000 International Units of vitamin A to 200,000 International Units of vitamin $D_3$; about 0.100 parts by weight di-alpha tocopheryl acetate; about 0.200 parts by weight ginseng America 1:1 propylene glycol; about 0.200 parts by weight imidazolidinyl urea; about 0.200 parts by weight triethanolamine; about 0.100 parts by weight of a solution of 1 percent FD&C Yellow #5 in water; and about 0.047 parts by weight 24 carat gold.

8. A lotion as set forth in claim 7, further made by adjusting the pH value of the lotion to between 5.5 and 6.0.

* * * * *